United States Patent [19]

Frigola Constansa et al.

[11] Patent Number: 4,797,483

[45] Date of Patent: Jan. 10, 1989

[54] PROCESS FOR OBTAINING 4-HYDROXY-2-METHYL-N-(2-PYRIDYL)-2H-1,2-BENZOTHIAZINE-3-CARBOXAMIDE 1,1-DIOXIDE

[75] Inventors: Jordi Frigola Constansa; Jose M. Ribalta Baro; Julio Campon Pardo, all of Barcelone, Spain

[73] Assignee: Induspol, S.A., Barcelona, Spain

[21] Appl. No.: 66,711

[22] Filed: Jun. 24, 1987

[30] Foreign Application Priority Data

Mar. 27, 1987 [ES] Spain ................................. 8700867

[51] Int. Cl.$^4$ ........................................... C07D 279/16
[52] U.S. Cl. ..................................................... 544/49
[58] Field of Search ......................................... 544/49

[56] References Cited

U.S. PATENT DOCUMENTS 3,303,189  2/1967  Loev ..................................... 544/49

Primary Examiner—Alan L. Rotman
Assistant Examiner—Robert C. Whittenbaugh
Attorney, Agent, or Firm—Fleit, Jacobson, Cohn & Price

[57] ABSTRACT

A process for obtaining 4-hydroxy-2-methyl-N-(2-pyridyl)-2H-1,2-benzothiazine-3-carboxamide 1,1-dioxide, which may be used as a non-steroidal analgesic and anti-inflammatory drug. The process comprises reacting saccharin sodium with isopropyl chloroacetate in dimethylformamide, reacting the resultant isopropyl 3-oxo-1,2-benzoisothiazoline-2-acetate 1,1-dioxide with sodium isopropylate in isopropanol to produce an intermediate which, when methylated in an aqueous-alcoholic basic medium with dimethyl sulfate, gives an intermediate compound which when condensed with 2-aminopyridine in xylene, yields 4-hydroxy-2-methyl-N-(2-pyridyl)-2H-1,2-benzothiazone-3-carboxamide 1,1-dioxide.

1 Claim, No Drawings

PROCESS FOR OBTAINING 4-HYDROXY-2-METHYL-N-(2-PYRIDYL)-2H-1,2-BENZOTHIAZINE-3-CARBOXAMIDE 1,1-DIOXIDE

By reacting saccharin sodium with isopropyl chloroacetate in dimethylformamide, isopropyl 3-oxo-1,2-benzoisothiazoline-2-acetate 1,1-dioxide is obtained which, by reaction with sodium isopropylate in isopropanol at temperatures between 60° C. and the boiling point of the solvent, for a time between 15 minutes and 3 hours, leads to a compound which, when methylated in an aqueous-alcoholic basic medium with dimethyl sulfate, gives an intermediate compound which, when condensed with 2-aminopyridine in xylene, yields 4-hydroxy-2-methyl-N-(2-pyridyl)-2H-1,2-benzothiazine-3-carboxamide 1,1-dioxide which may be used as a nonsteroidal analgesic and anti-inflammatory drug.

The present invention relates to a process for obtaining 4-hydroxy-2-methyl-N-(2-pyridyl)-2H-1,2-benzothiazine-3-carboxamide 1,1-dioxide, of formula I, a very pure, white product being obtained in high yield. The compound of formula I may be used as a non-steroid analgesic and anti-inflammatory agent.

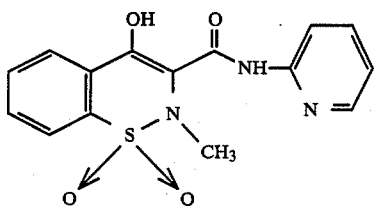

PRIOR ART

Abe et al. (J. Pharm. Soc. Japan, 1956, 76, 1058–63) were the first to apply the Gabriel Colman rearrangement to saccharin derivatives to obtain various 4-hydroxy-2H-1,2-benzothiazine 1,1-dioxides. Similarly, Zinnes (J. Org. Chem., 1965, 30, 2241) extended these studies to obtain new derivatives.

Lombardino (J. Med. Chem., 1971, 14, 1171–75) described the use of methyl 2-methyl-4-hydroxy-2H-1,2-benzothiazine-3-carboxylate 1,1-dioxide, of formula II (R=CH$_3$), as a starting substance for obtaining various 3-carboxamides. Subsequently, Rasmussen (J. Org. Chem., 1974, 39, 1554) described the use of the ethyl carboxylate derivatives of formula II (R=CH$_2$CH$_3$).

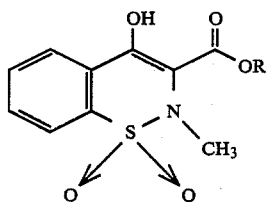

The compounds of formula II are obtained from saccharin or saccharin sodium by alkylation with the corresponding methyl or ethyl chloroacetate, subsequent Gabriel Colman rearrangement with the corresponding alkoxide and finally methylation on the nitrogen at the 2-position.

The yields described for the last two steps of each process are low (38% and 59% in the case of methyl; 69% and 71% in the case of ethyl) and the reaction conditions are critical, especially in the rearrangement.

Subsequently, Lombardino in U.S. Pat. No. 4,289,879 pointed out the difficulties of obtaining the final product of formula I with an acceptable color starting with the intermediate II (R=CH$_3$), due to the formation of the byproduct of formula III (R$^1$=CH$_3$),

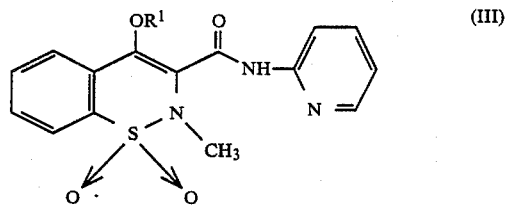

which is a highly colored compound difficult to remove by crystallization. In the said patent, the use of the intermediate of formula II (R=CH$_2$CH$_2$OCH$_3$), obtained via the known sequence in which saccharin is used as starting substance, is proposed as an alternative for solving this problem. This synthesis has the serious industrial disadvantage of significantly raising the cost of the product by using a more esoteric and less readily available intermediate.

DESCRIPTION OF THE INVENTION

According to the process described in the present invention, the compound I is manufactured by means of the following reaction sequence:

By reacting saccharin sodium with isopropyl chloroacetate in dimethylformamide, isopropyl 3-oxo-1,2-benzoisothiazoline-2-acetate 1,1-dioxide, of formula IV

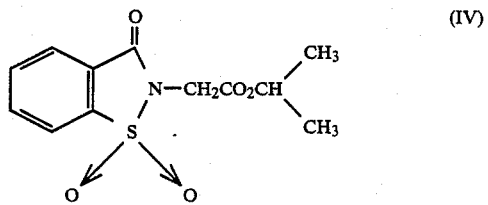

is obtained which, by Gabriel-Colman Rearrangement with sodium isopropylate in isopropanol, leads to the intermediate of formula V

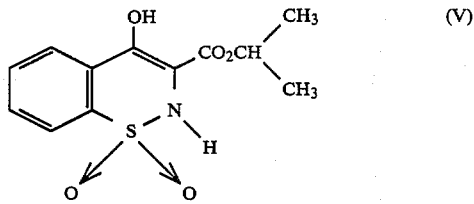

which is methylated in aqueous-alcoholic basic medium with a suitable agent such as methyl iodide or dimethyl sulfate to give the intermediate compound II [R=CH(CH$_3$)$_2$], which is finally condensed with 2-aminopyridine in a suitable solvent such as xylene or dimethylformamide to obtain the final product of formula I.

The synthesis of the compound IV in dimethylformamide is carried out at temperatures between 80° and 140° C., for a time which fluctuates between 2 and 5 hours. The rearrangement reaction of the compound of formula IV to obtain the compound of formula V is carried out at temperatures between 60° and the boiling point of the solvent, for a time between 15 minutes and 3 hours. The methylation of the compound V for a time of 2 to 5 hours, at temperatures between 5° C. and room temperature, gives rise to the formation of the compound II [R=CH(CH$_3$)$_2$]. By condensation of this latter compound with 2-aminopyridine at temperatures between 110° and 150° C., for a time of 12 to 48 hours, the desired product I is obtained.

Although the compound II [R=CH(CH$_3$$_2$] has been mentioned generically in some patents (e.g. U.S. Pat. No. 3,591,584), it has never been identified since neither spectroscopic nor melting point data appear in the chemical literature. The use of the isopropyl radical in the intermediate compounds in place of the more frequently used methyl and ethyl radicals has some significant advantages for the industrial production of the abovementioned compound I.

As may be verified in the experimental description of the process, excellent yields are obtained, and a very pure final product without problems of coloration. One of the possible impurities III [R$^1$=CH(CH$_3$)$_2$] has been synthesized [m.p. 102°–3° C.; IR (KBr):3330, 1680, 1355, 1175 cm$^{-1}$; $^1$H-NMR, δ, (CDCl$_3$: 1.41 (d,6H), 3.08 (s,3H), 4.46 (m,1H), 7.07 (m,1H), 7.78 (m,5H), 8.33 (m,2H), 10.24 (b,1H)] and it has been verified that it is not present in detectable amounts together with the compound I.

Similarly, the raw materials used are economical, dimethylformamide having been replaced in the rearrangement by isopropanol, which is a more readily available solvent that is much less contaminating by virtue of being recoverable. Moreover, it has the undoubted advantage of using the alkoxide prepared in situ without the need to remove the excess corresponding alcohol, thereby offering greater safety and less risk of contamination in respect of its use.

DESCRIPTION OF EMBODIMENTS

In order to facilitate understanding of the process which is the subject of the present invention, examples are provided of the different phases of the process but these should not be regarded as limiting.

EXAMPLE 1

Preparation of isopropyl 3-oxo-1,2-benzoisothiazoline-2-acetate 1,1-dioxide 23.3 kg (170.6 mol) of isopropyl chloroacetate are added to a solution at 50° C. of 40 kg (165.8 mol) of saccharin sodium dihydrate in 40 l of dimethylformamide. The mixture is heated to 120° C. and maintained for 3 hours at this temperature. The mixture is cooled and diluted with 240 l of water. Finally, the precipitate is centrifuged, washed with cold water and dried, 40.6 kg (86%) of a crystalline white solid, m.p. 112°–7° C. (118°–9° C. from isopropanol), being obtained.

Spectroscopic data:
IR (KBr): 1750; 1740; 1340; 1180 cm$^{-1}$.
$^1$H-NMR, δ, (CDCl$_3$): 1.27 (d,6H); 4.41 (s,2H); 5.11 (m,1H); 7.80–8.20 (m,4H).

EXAMPLE 2

Preparation of isopropyl 4-hydroxy-2H-1,2-benzothiazine-3-carboxylate 1,1-dioxide A solution of sodium isopropylate is prepared beforehand from 862 g (37.5 mol) of sodium and 18 l of isopropanol. To this solution at 80°–85° C., a hot solution of 4,250 g (15 mol) of isopropyl 3-oxo-1,2-benzoisothiazoline-2-acetate 1,1-dioxide in 12 l of isopropanol is added, adjusting the addition so that gentle refluxing is maintained. The mixture is maintained for 15 minutes at 80°–85° C., an orange precipitate gradually forming. The mixture is cooled under an atmosphere of nitrogen to about 45° C. and poured rapidly into a solution of 11 l of conc. HCl and 34 l of water. The precipitate obtained is centrifuged, washed with cold water and dried, 3,600 g (85%) of a white solid, m.p. 165°–7° C. (169°–170° C. from ethanol) being obtained.

Spectroscopic data:
IR (KBr): 3180; 1665; 1335; 1180 cm$^{-1}$.
$^1$H-NMR, δ, (CDCl$_3$): 1.39 (d,6H); 5.25 (m, 1H); 6.43 (b,1H); 7.65–8.13 (m,4H); 11.43 (b,1H).

EXAMPLE 3

Preparation of isopropyl 4-hydroxy-2-methyl-2H-1,2-benzothiazine-3-carboxylate 1,1-dioxide 1,425 ml (15 mol) of dimethyl sulfate are added at between 10° and 15° C. to a solution of 2,833 g (10 mol) of isopropyl 4-hydroxy-2H-1,2-benzothiazine-3-carboxylate 1,1-dioxide and 440 g (11 mol) of sodium hydroxide in 4 l of water and 11.3 l of isopropanol. The mixture is maintained with stirring for 4 hours at room temperature, diluted with 28 l of water and cooled to 0°–5° C. The precipitate obtained is centrifuged, washed with cold water and dried, 2.675 g (90%) of a white or slightly pink solid, m.p. 102°–3° C. (104°–5° C. from methanol), being obtained.

Spectroscopic data:
IR (KBr): 1660; 1350; 1160 cm$^{-1}$.
$^1$H-NMR, δ, (CDCl$_3$): 1.40, (d,6H); 2.96 (s,3H); 5.25 (m,1h); 7.65–8.10 (m,4H); 12.21 (s,1H).

EXAMPLE 4

Preparation of 4-hydroxy-2-methyl-N-(2-pyridyl)-2H-1,2-benzothiazine-3-carboxamide 1,1-dioxide A mixture of 74.3 g (0.25 mol) of isopropyl 4-hydroxy-2-methyl-2H-1,2-benzothiazine-3-carboxylate 1,1-dioxide and 25.7 g (0.32 mol) of 2-aminopyridine in 2,700 ml of xylene is maintained under reflux for 20 hours. During this time, approximately one third of the solvent is distilled off and is replaced, and finally the mixture is distilled to a final volume of 1,500 ml. The mixture is cooled to 0°–5° C. and filtered and the product washed with xylene. By crystallization with dichloroethane, 63 g (75%) of a crystalline white product, m.p. 198°–200° C. are obtained.

Spectroscopic data:
IR (KBr): 3410; 1645; 1360; 1180$^{-1}$.
$^1$H-NMR, δ, (CDCl$_3$): 2.95 (s,3H); 6.95–7.28 (dd,2H); 7.60–8.40 (m,6H); 8.85 (b,1H); 11.52 (b,1H).

We claim:

1. A process for manufacturing 4-hydroxy-2-methyl-N-(2-pyridyl)-2H-1,2-benzothiazine-3-carboxamide 1,1-dioxide, of formula I,

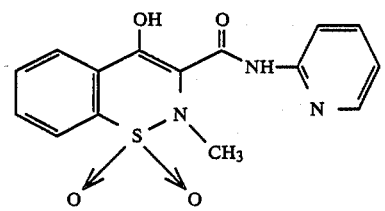 (I)

which comprises the following reaction sequence: reacting saccharin sodium with isopropyl chloroacetate in dimethylformamide to obtain isopropyl 3-oxo-1,2-benzoisothiazoline-2-acetate 1,1-dioxide, of formula II

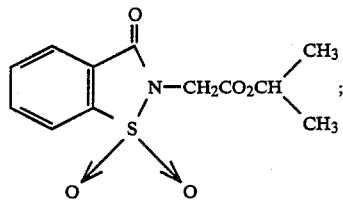 (II)

reacting the isopropyl 3-oxo-1,2-benzoisothiazoline-2-acetate 1,1-dioxide of formula II with sodium isopropylate in isopropanol at a temperature between 60° C. and the boiling point of the solvent, for a time between 15 minutes and 3 hours, to produce an intermediate of formula III

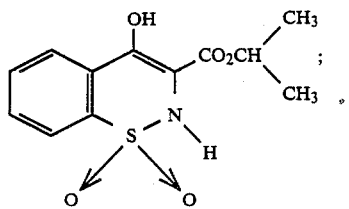 (III)

methylating the intermediate of formula III in an aqueous-alcoholic basic medium with dimethyl sulfate to produce an intermediate compound of formula IV

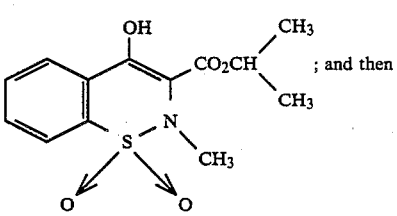 (IV) ; and then condensing the intermediate compound of formula IV with 2-aminopyridine in xylene to obtain a final product of formula I.

* * * * *